United States Patent [19]

Heady et al.

[11] Patent Number: 4,520,104
[45] Date of Patent: May 28, 1985

[54] PRODUCTION OF BUTANOL BY A CONTINUOUS FERMENTATION PROCESS

[75] Inventors: Robert E. Heady, Park Forest; Jeffrey R. Frankiewicz, Lombard, both of Ill.

[73] Assignee: CPC International Inc., Englewood Cliffs, N.J.

[21] Appl. No.: 442,806

[22] Filed: Nov. 18, 1982

[51] Int. Cl.$^3$ ............................................. C12P 7/16
[52] U.S. Cl. ..................................... 435/160; 435/842
[58] Field of Search ................................ 435/160, 842

[56] References Cited

U.S. PATENT DOCUMENTS 1,315,585  9/1919  Weizmann .
2,474,170  6/1949  Sulzbacher .
4,424,275  1/1984  Levy ..................................... 435/801

OTHER PUBLICATIONS

Dyr et al., In: "Continuous Cultivation of Microorganisms" (Prague Symposium), pp. 210–226, Prague: Czechoslovakia Academy of Sciences (1958).

Yamazaki et al., Butanol Fermentation, (Parts XXVII and XXVIII), Nippon Nogei Kagaku Kaishi, vol. 32, pp. 758–770 (1958).

"Alcohol Fuels Process R/D Newsletter", pp. 38–39, Winter 1980.

Malek et al., "Theoretical and Methodological Basis of Continuous Culture of Microorganisms", pp. 611–613, Prague: Czechoslovakia Academy of Sciences (1966).

Primary Examiner—Sam Rosen
Attorney, Agent, or Firm—Stanley M. Parmerter

[57] ABSTRACT

An improved process for the continuous production of butanol by fermentation of carbohydrates with *C. acetobutylicum* is disclosed. This process combines continuous inoculum production at a high dilution rate and cycling the fermentation broth through a material which adsorbs butanol whereby a vigorous cell population is maintained in the fermentation reactor for extended periods of time.

9 Claims, No Drawings

PRODUCTION OF BUTANOL BY A CONTINUOUS FERMENTATION PROCESS

FIELD OF THE INVENTION

This invention relates to a method for the production of butanol and smaller amounts of other solvents by a continuous fermentation process.

BACKGROUND OF THE INVENTION

The fermentation of carbohydrates to form butanol and acetone by *Clostridium acetobutylicum* (hereafter abbreviated *C. acetobutylicum*) was disclosed by Weizmann in U.S. Pat. No. 1,315,585. For many years, this process was used for the preparation of acetone and butanol, and a certain amount of ethyl alcohol was obtained as a by-product.

Eventually, the microbial process was displaced by chemical processes which provide the same products using cheap fossil fuel raw materials. However, the gradual depletion of petroleum fossil fuel with the resultant increase in prices of petrochemical feedstocks has revived interest in the fermentation reaction that uses carbohydrates, which are renewable raw materials.

One problem encountered in the earlier commercial production of butanol by the fermentation process was the long time before the microorganism began to produce appreciable quantities of butanol. These processes typically used a parent culture that was stored as spores. In order to initiate a fermentation, the spores were placed in an aqueous medium containing various nutrients, subjected to a thermal shock and then passed through three growth stages in vessels of increasing size before they were used to inoculate the fermentation tank. This process required about 3 days for inoculum development plus an additional 2 to 3 days to complete the fermentation.

A second problem with batch fermentations was the instability of the microorganism in concentrations of butanol about about 1% by weight. The cells tend to die rapidly after the concentration of the product reaches this level. Thus, only low concentrations of product could be obtained in the fermentation broth. Such a process requires a large fermentation capacity to produce practical amounts of solvent, and it is expensive to recover the solvents from the fermentation broth due to their low concentrations.

Various workers have suggested that if the butanol fermentation were conducted in a continuous process, some of the difficulties associated with the batch mode might be overcome. Such a process would make more efficient use of the fermentors by eliminating the unproductive time between batches when the fermentor has to be emptied, cleaned, filled, sterilized, and cooled. In the past, such processes have been of little usefulness because of culture instability, contamination problems, or low volumetric productivity of butanol.

The term "volumetric productivity" as used in this application refers to the amount of a product produced in a continuous fermentation per unit volume of fermentation broth per unit of time. It is commonly reported in grams per liter-hour, abbreviated g/l-hr.

One report of continuous butanol fermentation studies was given by Dyr, et al, in: Continuous cultivation of Microorganisms (Prague Symposium), pp. 210–226, Prague: Czechoslovakia Academy of Sciences (1958). By means of a multistage fermentation system and by adjusting the dilution rate, he was able to overcome some of the problems of culture instability, but the highest concentration of butanol reported indicated a volumetric productivity of only about 0.24 g/l-hr for the system.

Another method which has been proposed to avoid the culture instability problem associated with continuous fermentations is the use of spores or nongrowing cells of the microorganism immobilized in a gel. Häggström, et al, International application PCT/SE80/00231. Although this technique does provide a means for conducting a continuous fermentation for comparatively long times, it uses an expensive material and process for immobilizing the microorganism. The reported volumetric productivity of butanol by this method is about 0.33 g/l-hr.

A process has now been discovered which avoids the problems inherent in the batch process and which permits the fermentation to be carried out in a continuous process for a number of days without culture deterioration. In addition, this process can be carried out using raw materials readily available from the corn wet-milling industry, and it produces butanol at a much greater volumetric productivity. Furthermore, it provides as an integral part of the process an economical means for the concentration and recovery of the butanol produced in the fermentation.

SUMMARY OF THE INVENTION

In accordance with the invention, there is provided a process for producing butanol by continuous fermentation of a carbohydrate with a strain of *C. acetobutylicum*. This process comprises continuously producing inoculum of the strain at a dilution rate that minimizes butanol contact with the inoculum to provide a high population of healthy cells of the microorganism in the inoculum. The inoculum is continuously supplied to a fermentation medium. A portion of the fermentation medium is continuously cycled through butanol-adsorbing material at a rate sufficient to maintain a less than about 1% by weight butanol concentration in the fermentation medium. The butanol is then isolated by desorbing it from the material on which it is adsorbed.

DETAILED DESCRIPTION OF THE INVENTION

The fermentation process of this invention involves the fermentation of a carbohydrate by a strain of *C. acetobutylicum* to form butanol and lesser amounts of acetone and other solvents. In general, any strain of *C. acetobutylicum* which forms primarily butanol can be employed. A useful strain for the practice of this invention is the strain of *C. acetobutylicum*, ATCC 4259, which is available from the American Type Culture Collection, Rockville, Maryland. A preferred strain for the use of this invention is the asporogenic strain of *C. acetobutylicum*, ATCC 39236, which is described in detail in a copending patent application, Ser. No. 442,805, titled "Improved Strain of *Clostridium acetobutylicum* and Process for Its Preparation", filed Nov. 18, 1982, the disclosure of which is incorporated herein by reference in its entirety.

The carbohydrate used in the practice of this invention can be any carbohydrate that is fermented by the strain of *C. acetobutylicum* used. These carbohydrate sources include solubilized starches and sugar syrups as well as glucose or sucrose in pure or crude forms. The fermentation medium should also contain nutrients and other growth factors needed for growth and reproduction of the microorganism employed.

When the strains of *C. acetobutylicum* are ATCC 4259 or ATCC 39236, a suitable medium for carrying out the continuous process of this invention comprises an aqueous solution of a low D.E. (dextrose equivalent) starch hydrolyzate to which has been added a small amount (from about 0.5% to about 2% by weight, dry basis) of corn steep liquor. Low D.E. (about 5 D.E. to about 20 D.E.) starch hydrolyzates produced by the partial hydrolysis of starch, are readily available from the corn milling industry. Likewise, corn steep liquor, which is produced when corn is steeped in a dilute solution of sulfur dioxide, is available from the corn wet-milling industry. When the medium used for carrying out the continuous fermentation comprises only a low D.E. starch hydrolyzate and corn steep liquor, growth of the microorganism is enhanced by the periodic addition to the fermentor of corn gluten slurry. This slurry as well as the other two ingredients are readily available raw materials obtained from the wet milling of corn and thus provide an economical and renewable source for the carbohydrate and all of the other nutrients needed for the growth of the microorganism.

The fermentation process of the present invention is initiated by inoculating sterile medium in an inoculum-producing reactor with a seed culture of a strain of *C. acetobutylicum*. Fermentation is allowed to continue until a good growth of cells is developed. The reactor is then operated as a continuous reactor with sterile medium flowing into the reactor and medium plus cells flowing out of the reactor into a fermentation reactor. By this means, an inoculum is produced and fed continuously into the fermentation reactor where butanol production takes place.

The continuous inoculum-producing reactor is run at a dilution rate which prevents the buildup of solvents in the medium and produces vigorous healthy cells of the culture with little exposure to butanol. In the description of this invention, the words "dilution rate" designate the value obtained by dividing the flow rate of the medium through the reactor in volume units per hour by the operating volume of the reactor measured in the same volume units. It has the dimensions of per hour.

By operating the inoculum-producing reactor at a dilution rate of from about 0.2 to about 0.5 per hour, healthy cells with little exposure to butanol are formed continuously and passed from the reaction vessel to the fermentation reactor where solvent production proceeds. The fermentation reactor is also operated in a continuous mode but at a much lower dilution rate than that in the vessel in which the inoculum is produced.

The proper dilution rate in the fermentation reactor depends on the concentration of carbohydrate in the fermentation medium and the rate at which the medium is cycled through butanol-adsorbing material. For an efficient fermentation, the dilution and recycle rates are adjusted so that the carbohydrate is essentially all consumed. In the examples, the dilution rate was held constant at 0.03 per hour and the recycle rate was varied with the concentration of carbohydrate in the medium.

It is possible to run the continuous inoculum production in two or more continuous reaction vessels operated in series. The important condition is that each of these inoculum-producing vessels must be operated at a dilution rate such that healthy, vigorous growing cells are produced in a continuous manner with little exposure to butanol.

Inoculum formation and solvent production are carried out at a temperature of from about 34° C. to about 40° C. and at a pH of from about 4.5 to about 5.5. The reactions are run under anaerobic conditions using medium which has been sterilized by heat or other means well known in the fermentation art.

The continuous fermentation reaction is connected to a device, such as a column, which contains material that adsorbs butanol. Broth from the fermentation reactor is cycled through this device and back to the reactor on a continuous basis to remove a large portion of the butanol from the fermentation medium. The fermentation broth is passed through the adsorbing material at such a rate that the butanol concentration in the fermentation reactor is maintained at a level below about 1% by weight, preferably below about 0.8% by weight.

The adsorbent material used in the device connected to the fermentation reactor can be any material that adsorbs butanol without interfering with the fermentation reaction. Prior workers have noted that activated carbon adsorbs butanol. Sulzbacker, U.S. Pat. No. 2,474,170, used this material to remove solvents from a filtered broth after fermentation. Yamazaki, et al, Nippon Nogei Kagaku Kaishi, 32, 758–770 (1958), reported that suspension of a bag of activated carbon in a batch fermentation could be used to enhance the conversion of sugar to butanol. However, a recent report from the Massachusetts Institute of Technology (Alcohol Fuels Process R/D Newsletter, pp. 38–39, Winter 1980) states that carbon interferes with the fermentation and is undesirable for this purpose.

We have found that granular activated carbon is a suitable butanol adsorbent in our process. Other possible adsorbents are molecular sieves and adsorbent resins. A particularly suitable adsorbent is PCB Pittsburgh activated carbon, 12–30 mesh (U.S. Standard Sieve size with sieve openings of 1.68 mm to 0.59 mm), available from the Calgon Corporation, Pittsburgh, Pa.

A periodic reversal of the direction of flow of the fermentation broth through the device containing the adsorbent material aids in maintaining good flow through the device. By this means, most of the cells which may have accumulated in the adsorptive material are returned to the fermentation reactor.

Passing the fermentation broth through the adsorptive material removes butanol and other substances toxic to *C. acetobutylicum*. By this means, vigorous fermentation is promoted with nearly complete fermentation of carbohydrate even when it is present in concentrations as high as 15% in the medium.

The use of an adsorptive material, such as activated carbon, to remove the butanol and other solvents from the fermentation broth also offers an economical means for recovery of the butanol. When the carbon is saturated with butanol, the butanol can be desorbed from the carbon by means of acetone or other vapors as disclosed in patent application U.S. Ser. No. 327,849, filed Dec. 7, 1981, the disclosure of which is incorporated herein by reference in its entirety.

Effluent from the continuous fermentation reactor, which contains small amounts of butanol and other solvents, can be treated by conventional means for recovery of these mutants.

The following examples further describe the embodiments of this invention. All parts are by weight and all percentages are by weight unless expressly stated to be otherwise.

Solvent concentrations were determined using high-performance liquid chromatography (HPLC). Components were analyzed chromatographically by elution with 0.006 N $H_2SO_4$ from a cation-exchange resin in the hydrogen form. The eluted components were detected by means of a differential refractometer, plotted on a recorder and quantitated using an electronic integrator. The area under the curve which represents the concentration of each component is reported as a percentage of the total area. The general procedure is that given in "Analysis of Carbohydrate Mixtures by Liquid Chromatography", *Am. Soc. Brew. Chem. Proc.*, 1973, pp. 43–46. The separations were made on a 1-foot HPX-87 column in the hydrogen form, available from Bio-Rad Laboratories, Richmond, Calif.

Residual total carbohydrate (RTC) in the fermentation medium was measured by the phenol/sulfuric acid method. This is described in detail by Dubois, et al, "Colorimetric Method Determination of Sugars and Related Substances", *Anal. Chem.*, 28, 350–356 (1956).

EXAMPLE 1

A culture of *C. acetobutylicum*, ATCC 4259, was obtained from the American Type Culture Collection, Rockville, Md., and maintained in a sporulated state on a mixture of soil, sand, and calcium carbonate. Inoculum for initiating a continuous culture was developed in a 125-ml Erlenmeyer seed flask containing 75 ml of an aqueous medium consisting of 6% dry basis of a 10 D.E. starch hydrolyzate (available from the Grain Processing Company, Muscatine, Iowa, as Maltrin M-100) and 0.75% dry basis of corn steep liquor available from the Corn Products Unit of CPC International Inc., Englewood Cliffs, N.J., as Code E801). The pH of the medium was adjusted to 6.6 with 4 N NaOH solution before it was sterilized by heating in an autoclave at 121° C. for 20 minutes. The cooled sterile medium in the seed flask was inoculated with 5 ml of a heat shocked suspension of spores of the culture contained in the same medium. Heat shocking was accomplished by first suspending about 0.5 g of a soil-spore suspension in 10 ml of the seed medium. The suspension was then placed in boiling water for 90 seconds and rapidly cooled to room temperature. The seed flask with inoculated medium was incubated in an anaerobic chamber for 21 hours at 35° C.

A continuous fermentation was conducted in a three-stage fermentation system under anaerobic conditions. The first- and second-stage fermentors were standard 2-liter New Brunswick Bioflow, Model C-30 vessels containing bottom-driven magnetic stirrers. The third-stage fermentor was a 14-liter vessel with a bottom-driven magnetic stirrer. The operating volumes were 725 ml, 1450 ml and 9.5 liters respectively, in the three fermentors. Each fermentor was agitated at a rate of 200 revolutions per minute. The aqueous medium used for the fermentations contained 7.5% by weight dry basis of 10 D.E. starch hydrolyzate and 0.75% by weight dry basis of corn steep liquor adjusted to a pH of 5.0–5.1 with 4 N NaOH. Fermentation was initiated by inoculating the first-stage fermentor with 75 ml of seed culture after first filling it with growth medium sparged with $CO_2$ (anaerobic grade) for 30 minutes and adjusted to a pH of 6.1 to 6.2 with concentrated ammonium hydroxide. The first-stage fermentor was held at 37° C. for 4 hours after inoculation before medium flow in and out of the fermentor was begun. All of the mixture flowing from the first-stage fermentor was passed into the second-stage fermentor which had been previously filled with 850 ml of sterile medium of the same composition as that added to the first fermentor. Fresh sterile medium was also added to the second-stage fermentor at the same rate as the effluent from the first-stage fermentor passed into it. The effluent from the second-stage fermentor was passed into third-stage fermentors. The temperature of all fermentors was controlled at $37° \pm 1°$ C. The pH of the first-stage fermentor was controlled by adding ammonium hydroxide so that the pH did not fall below 5.0 and the pH of the second-stage fermentor was controlled by the addition of 4 N NaOH so that its pH did not fall below 5.0. The pH was not controlled in the third-stage fermentors. When the third-stage fermentors were filled to the desired level (9.5 liters) with the effluent from the second-stage fermentor, the culture broth was allowed to flow from them at the same rate as it entered from the second-stage fermentor. The flow rates were so adjusted that the dilution rates in the first-stage and second-stage fermentors (which produced inoculum) were about 0.45 per hour, and in the third-stage fermentors were about 0.031 per hour. These flow rates allowed the second-stage fermentor to feed two third-stage fermentors.

The medium in one third-stage fermentor was supplemented by adding once every 24 hours a 10% aqueous slurry containing 25 g, dry basis, of corn gluten. This slurry was adjusted to pH 5.2 with 4 N NaOH and sterilized before the addition.

At periodic intervals, samples of broth from both third-stage fermentors were centrifuged to remove solids and the supernatant liquids were analyzed. The results given in Table I show that butanol is being produced in both fermentors and that the fermentor containing added gluten contains somewhat less residual total carbohydrate.

TABLE I

CONTINUOUS FERMENTATION (THREE STAGES)

| | Fermentor With Added Gluten | | | Fermentor Without Added Gluten | | |
|---|---|---|---|---|---|---|
| Time (hrs) | pH | RTC[a] (mg/ml) | Butanol (g/100 ml) | pH | RTC[a] (mg/ml) | Butanol (g/100 ml) |
| 21 | 4.8 | 67.3 | 0.01 | 4.6 | 59.3 | 0.02 |
| 27 | 4.5 | 61.6 | 0.03 | 4.2 | 62.7 | 0.05 |
| 48 | 4.8 | 54.6 | 0.40 | 4.8 | 43.3 | 0.10 |
| 71 | 5.0 | 39.5 | 0.74 | 4.9 | 48.3 | 0.53 |
| 93 | 5.1 | 31.0 | 0.92 | 5.0 | 48.2 | 0.70 |
| 99 | 5.0 | 26.7 | 0.97 | 5.1 | 39.3 | 0.73 |
| 117 | 4.9 | 24.3 | 1.01 | 5.1 | 35.2 | 0.80 |
| 123 | 4.9 | 21.6 | 1.01 | 5.1 | 34.4 | 0.88 |
| 141 | 4.7 | 26.0 | 0.88 | 5.1 | 32.8 | 0.93 |
| 146 | 4.7 | 28.2 | 0.83 | 5.1 | 30.2 | 0.93 |

[a]RTC = residual total carbohydrate.

When the continuous fermentation had progressed for 146 hrs, a portion of the fermentation broth from the third-stage fermentor containing added gluten was passed upward through about 2.1 kg of activated carbon contained in a cylindrical stainless steel column, 122 cm long with an internal diameter of 7.29 cm. Passage was at a rate of about 720 ml per hour through the column with the effluent from the top of the column being returned to the fermentor at the same rate. The carbon used in the column was PCB Pittsburgh activated carbon, 12–30 mesh (U.S. Standard Sieve size with sieve openings of 1.68 mm to 0.59 mm), available from the Calgon Corporation, Pittsburgh, Pa. Every 2 hours the direction of flow of the fermentation broth through the carbon column was reversed for 12 minutes and run at the rate of 50 ml per minute in order to return to the fermentor any cells which had accumulated at the bottom of the column. When the carbon in the column became saturated with butanol, it was replaced with a column containing fresh carbon. The other third-stage fermentor was run without a carbon column. Test results are given in Table II where the time is the elapsed time from the start of the original fermentation.

These results show that cycling the fermentation broth through a carbon column is effective in reducing the butanol concentration in the broth. They further show that the fermentation in the fermentor with the broth cycled through the carbon column utilizes the carbohydrate much more completely than does the fermentation in the fermentor without the carbon column even though both fermentors are operated at the same dilution rate.

TABLE II

| | CONTINUOUS FERMENTATION (THREE STAGES) | | | | |
|---|---|---|---|---|---|
| | Fermentor With Carbon Column | | | Fermentor Without Carbon Column | |
| Time (hrs) | pH | RTC$^a$ (mg/ml) | Butanol (g/100 ml) | pH | RTC$^a$ (mg/ml) | Butanol (g/100 ml) |
| 171 | 4.7 | 21.3 | 0.35 | 5.0 | 24.6 | 1.06 |
| 195 | 4.5 | 12.6 | 0.46 | 4.8 | 22.3 | 1.00 |
| 220.5 | 4.7 | 2.2 | 0.43 | 4.7 | 35.7 | 0.71 |
| 260 | 4.7 | 1.9 | 0.38 | 4.9 | 22.4 | 1.01 |
| 290.5 | 5.2 | 1.5 | 0.56 | 4.8 | 25.0 | 0.97 |
| 332 | 4.9 | 1.7 | 0.43 | 4.9 | 24.2 | 0.92 |
| 356 | 5.0 | 2.5 | 0.39 | 4.9 | 24.2 | 0.99 |

$^a$RTC = residual total carbohydrate.
$^b$Flow of fermentation broth through carbon column begun.

The continuous fermentation was run successfully for 40 days. When carbohydrate concentration in the medium fed to the fermentors was increased to 10% and 15%, the rate of flow through the carbon column was increased to about 840 ml/hr and 1500 ml/hr respectively. At the 15% carbohydrate concentration, the fermentation connected to the carbon column consumed over 90% of the carbohydrate, indicating a volumetric productivity of about 0.9 g/l-hr while the fermentation without this column consumed only about 30% of the carbohydrate with a volumetric productivity of 0.3 g/l-hr.

EXAMPLE 2

The general process of Example 1 was repeated except that the continuous fermentation was conducted in a two-stage fermentation system and the concentration of starch hydrolyzate in the medium was increased to 10%. The first-stage fermentor was the standard 2-liter New Brunswick Bioflow, Model C-30 vessel operated at an operating volume of 1450 ml and the second-stage fermentor was the 14-liter vessel run at an operating volume of 9.5 liters. The dilution rate in the first-stage fermentor was held at 0.23 per hour, while the dilution rate in the second-stage was 0.031 per hour. A 10% corn gluten slurry was added to the second-stage fermentor at a rate of about 20 ml/hr. The fermentation broth in the single second-stage fermentor was cycled through a carbon column like that described in Example 1. About 900 ml/hr was passed into the column, 600 ml/hr flowing from the column was returned to the fermentor and the rest was discarded. The butanol concentration in the first-stage fermentor never exceeded 0.05 g/100 ml. There was very little butanol in the effluent from the carbon column. Analyses of the filtered broth from the second-stage fermentor given in Table III show that the continuous process can be operated using only one stage for inoculum development.

TABLE III

| CONTINUOUS FERMENTATION (TWO STAGES) | | | |
|---|---|---|---|
| Time (hrs) | pH | RTC$^a$ (mg/ml) | Butanol (g/100 ml) |
| 48 | 4.4 | 114.5 | 0.20 |
| 76 | 4.9 | 88.0 | 0.61 |
| 100 | 4.9 | 73.9 | 0.86 |
| 124 | 4.9 | 56.0 | 0.79 |
| 170 | 4.8 | 25.5 | 1.23 |
| 220 | 5.0 | 54.8 | 0.93 |
| 262 | 4.9 | 30.9 | 0.86 |
| 286 | 5.0 | 11.1 | 0.98 |
| 310 | 5.1 | 4.9 | 0.93 |
| 316 | 5.1 | 7.2 | 0.93 |
| 337 | 5.0 | 4.1 | 0.88 |
| 358 | 5.0 | 5.4 | 0.80 |

$^a$RTC = residual total carbohydrate.

Thus, it is apparent that there has been provided, in accordance with this invention, an improved continuous process for the production of butanol by a fermentation reaction. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for producing butanol by continuous fermentation of a carbohydrate with a strain of *C. acetobutylicum* wherein the improvement comprises:
   continuously in a separate reactor producing inoculum of said strain at a dilution rate that minimizes butanol contact with said inoculum;
   continuously supplying said inoculum to the fermentation medium;
   continuously cycling a portion of the fermentation medium through a butanol-adsorbing material at a rate sufficient to maintain a less than about 1% by weight butanol concentration in the fermentation medium; and
   isolating the butanol by desorbing it from the butanol-adsorbing material.

2. The process of claim 1 characterized in that the inoculum is continuously produced at a dilution rate of from about 0.2 per hour to about 0.5 per hour.

3. The process of claim 1 characterized in that the inoculum is continuously produced at a dilution rate that maintains the butanol concentration below about 0.05 g/ml of the inoculum.

4. The process of claim 1 wherein the inoculum producing step is carried out in two continuous reaction vessels operated in series.

5. The process of claim 1 characterized in that the fermentation medium is maintained at a pH of from about 4.5 to about 5.5.

6. The process of claim 1 characterized in that the fermentation medium is maintained at a temperature of from about 34° C. to about 40° C.

7. The process of claim 1 characterized in that the butanol concentration in the fermentation medium is maintained at a level below about 0.8% by weight.

8. The process of claim 1 characterized in that the butanol-adsorbing material is granular activated carbon.

9. The process of claim 1 characterized in that the strain of *C. acetobutylicum* is selected from the group consisting of ATCC 4259 and ATCC 39236.

* * * * *

UNITED STATES PATENT AND TRADEMARK OFFICE
CERTIFICATE OF CORRECTION

PATENT NO. : 4,520,104

DATED : May 28, 1985

INVENTOR(S) : Robert E. Heady and Jeffrey R. Frankiewicz

It is certified that error appears in the above–identified patent and that said Letters Patent are hereby corrected as shown below:

Column 1, line 40, first "about" should read --above--.
Column 1, line 64, "cultivation" should read --Cultivation--.
Column 2, line 9, "application" should read --Application--.
Column 4, line 58, "patent application" should read --Patent Application--.
Column 4, line 64, "mutants" should read --solvents--.
Column 7, Table II, in heading, Fermentor With Carbon Column, after "Column" insert superscript --b--.
Column 7, Table II, Footnote b, after "begun" insert --at 146 hrs--.

Signed and Sealed this

Twenty-second Day of October 1985

[SEAL]

Attest:

DONALD J. QUIGG

Attesting Officer

Commissioner of Patents and Trademarks—Designate